United States Patent
Masere et al.

(10) Patent No.: US 11,104,626 B2
(45) Date of Patent: Aug. 31, 2021

(54) HYDROXYLATED QUINONE ANTIPOLYMERANTS AND METHODS OF USING

(71) Applicant: Ecolab USA Inc., St. Paul, MN (US)

(72) Inventors: Jonathan Masere, Richmond, TX (US); Russell P. Watson, Idaho Falls, ID (US); Ashish Dhawan, Aurora, IL (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 16/721,297

(22) Filed: Dec. 19, 2019

(65) Prior Publication Data

US 2020/0199048 A1 Jun. 25, 2020

Related U.S. Application Data

(60) Provisional application No. 62/782,755, filed on Dec. 20, 2018.

(51) Int. Cl.
*C07C 7/20* (2006.01)
*C07C 67/62* (2006.01)

(52) U.S. Cl.
CPC ............... *C07C 7/20* (2013.01); *C07C 67/62* (2013.01)

(58) Field of Classification Search
CPC ........... C07C 67/62; C07C 7/20; C07C 15/46; C07C 69/54; C07C 50/28; C08F 112/08; C08F 2/40; C08F 2410/01; C09K 15/04
See application file for complete search history.

(56) References Cited

U.S. PATENT DOCUMENTS

| | | | |
|---|---|---|---|
| 3,651,036 A | 3/1972 | Watanabe et al. | |
| 3,816,276 A | 6/1974 | Ichiki et al. | |
| 4,105,510 A | 8/1978 | Tago et al. | |
| 4,410,644 A | 10/1983 | Bunyan | |
| 5,241,022 A * | 8/1993 | Watanabe | C08F 2/004 252/180 |
| 5,648,573 A | 7/1997 | Arhancet et al. | |
| 5,728,872 A | 3/1998 | Riemenschneider | |
| 5,773,674 A | 6/1998 | Arhancet et al. | |
| 9,133,288 B2 | 9/2015 | Loyns et al. | |
| 2002/0037958 A1 * | 3/2002 | Benage | C07C 7/20 524/714 |
| 2014/0194559 A1 | 7/2014 | Price et al. | |

FOREIGN PATENT DOCUMENTS

| | | | |
|---|---|---|---|
| GB | 2110722 | * | 6/1983 |
| GB | 2110722 A | | 6/1983 |
| JP | 2002-284717 | * | 10/2002 |
| JP | 2009-045897 | * | 3/2009 |
| WO | 0140149 A2 | | 6/2001 |
| WO | 2013027042 A1 | | 2/2013 |

OTHER PUBLICATIONS

JP2002-284717 translated (Year: 2002).*
Frank et al. (The Relative Efficiency of Some Polymerization Inhibitors, JACS, 68, p. 908, Published 1946) (Year: 1946).*
JP2009-045897 translated (Year: 2009).*
Gulaboski, R., et al., (2013) "Hydroxylated derivatives of dimethoxy-1,4-benzoquinone as redox switchable earth-alkaline metal ligands and radical scavengers", Scientific Report 3:1865, pp. 1-8.
Qin, Y., et al., (2015) "Bioinspired Organocatalytic Aerobic C—H Oxidation of Amines with an ortho-Quinone Catalyst", Org. Lett., 17(6):1469-1472.
Misiolek, A. W., et al., (2009) "Building Blocks for Molecule-Based Magnets: Radical Anions and Dianions of Substituted 3,6-Dimethylenecyclohexane-1,2,4,5-tetrones as Paramagnetic Bridging Ligands", Inorganic Chemistry, 48:9005-9017.
Verter, H. S., et al. (1966) "Preparation of 2,5-Bis(alkylamino)-3,6-dimethoxy-p-benzoquinones", J. Org. Chem., 31 (3):987-988.
Pan et al. (2016) "2,5-Dimethoxy-1,4-Benzoquirione (DMBQ) as Organic Cathodefor Rechargeable Magnesium-Ion Batteries", Journal of The Electrochemical Society, 163(3):A580-A583.

* cited by examiner

*Primary Examiner* — Yevgeny Valenrod
*Assistant Examiner* — Blaine G Doletski
(74) *Attorney, Agent, or Firm* — Kagan Binder, PLLC (57) ABSTRACT

Described are methods and compositions for inhibiting polymerization of a monomer (e.g., styrene) composition using a hydroxylated quinone antipolymerant. The hydroxylated quinone antipolymerant can be used with little or no nitroxyl group containing antipolymerant yet still provide excellent antipolymerant activity in a monomer-containing composition.

20 Claims, 2 Drawing Sheets

FIG. 1

FIG. 2

HYDROXYLATED QUINONE ANTIPOLYMERANTS AND METHODS OF USING

CROSS REFERENCE TO RELATED APPLICATION

This application claims the benefit of U.S. Provisional Patent Application Ser. No. 62/782,755 filed Dec. 20, 2018, the disclosure of which is incorporated by reference herein in its entirety.

TECHNICAL FIELD

The invention is directed to compositions and use of hydroxylated quinone antipolymerant compounds for preventing premature polymerization of monomers.

BACKGROUND

The high-temperature processing of hydrocarbon stream laden with ethylenically unsaturated monomers like styrene, isoprene, butadiene, for instance, can be very challenging. In various chemical industrial processes, the use of high temperatures to purify said monomers can lead to unwanted and problematic polymers. These vinylic monomers undesirably polymerize through radical polymerization especially at elevated temperatures. Similarly, transportation and storage of hydrocarbon streams containing vinylic species can lead to premature polymerization unless antipolymerants are added to said streams. The polymer thus formed can precipitate from solution to foul the process equipment. Removing the foulants becomes necessary. The physical removal or cleaning of the fouled equipment is often expensive. These undesirable polymerization reactions also result in a loss in the production efficiency and the consumption of valuable products. Undesired polymerization reactions are particularly problematic in compositions having vinyl aromatic monomers To prevent undesired polymerization reactions, free-radical polymerization inhibitors as antipolymerants are often added to process streams or stored compositions. However, these compounds are generally consumed quite rapidly. For example, in cases of emergency due to a mechanical or processing problems and where more inhibitor cannot be added, previously added inhibitor will be rapidly consumed. Subsequently, unwanted polymerization reactions will then rapidly recur.

Examples of polymerization inhibitors known in the art include dialkylhydroxylamines, such as hydroxypropylhydroxylamine (HPHA), and stable nitroxide free radicals. Other inhibitors include N,N'-dialkylphenylenediamines, N,N'-diarylphenylenediamines and N-aryl-N'-alkylphenylene-diamines. Quinone diimide compounds are also another class of inhibitors. However, nitroxide-containing compounds can release $NO_x$, making their use undesirable in some situations.

Other types of antipolymerant compounds often referred to as "retarders" slow down the rate of polymerization reactions. However, they are often not as effective as polymerization inhibitors, particularly stable nitroxide free radicals. Polymerization retarders, however, are usually not consumed as quickly as polymerization inhibitors so they tend to be more useful in cases of emergency shutdowns.

Retarders such as sulfur and dinitrophenol (DNP) compounds exemplified by 2,6-dinitrophenol, 2,4-dinitrocresol, and 2-sec-butyl-4,6-dinitrophenol (DNBP), were initially used. However DNP and sulfur retarders release $NO_X$ and $SO_X$ emissions, making their use problematic. Furthermore, DNP-based retarders are highly toxic such that the safety of personnel handling DNP-based antipolymerants is a major concern.

One class of compounds designed to function as a safer substitute for DNP retarders is based on quinone methide chemistry. Quinone methides slow the rate of polymer formation under static conditions and do not need to be frequently re-fed into the process stream. Some quinone methide compounds, however, do not exhibit good stability. Examples of quinone methide compounds are in U.S. Pat. Nos. 4,003,800, 5,583,247, and 7,045,647. The production of styrene typically involves the use of both an inhibitor (e.g., a nitroxide-containing inhibitor such as TEMPO) and a retarder (e.g., a quinone methide). While it is desired in various styrene production situations to eliminate the nitroxide-containing inhibitor, the use of only a retarder has been found to provide insufficient polymerization inhibition, making it difficult to eliminate or minimize inhibitor use.

Technical challenges remain in this area of technology relating to efficacy of compounds used to inhibit or slow polymerization reactions, as well as stability and safety concerns. In spite of the concerns over toxicity, DNP-based antipolymerants remain the most efficient retarders available. Out of safety concerns, there is a need for antipolymerants that are at least as efficacious as DNP-type retarders, but non-toxic.

SUMMARY

The current disclosure is directed to compositions and methods that include or utilize a hydroxylated quinone antipolymerant to inhibit the polymerization of ethylenically unsaturated monomers like styrene and butadiene in various processes and situations, such as purification, fractionation, separation, compression, transportation, and storage of various monomer-containing compositions. Advantageously, the hydroxylated quinone antipolymerant can be used without, or with very little, other antipolymerants, yet it still provides excellent ability to inhibit polymerization of monomers in solution.

The use of the inventive hydroxylated quinone antipolymerant compositions mitigates the fouling of process, transportation and storage equipment. In turn, polymer contamination of purified monomer products can be drastically reduced and maintenance costs of said equipment minimized. Further, it can also be used to inhibit monomer polymerization in compositions without requiring other types of polymerization inhibitors such as nitroxyl-based antipolymerants.

In embodiments, the disclosure provides a method for inhibiting the polymerization of monomers in a composition comprising polymerizable monomers, or compounds capable of forming polymerizable monomers. The method includes a step of adding a hydroxylated quinone antipolymerant to a composition comprising polymerizable monomer or a compound capable of forming a polymerizable monomer, the antipolymerant being a compound of Formula I:

(I)

wherein at least two of —R¹, —R², —R³, and —R⁴ are —OR¹⁰, wherein R¹⁰ is selected from the group consisting of hydrogen, alkyl, aryl, alkyl aryl, and aryl alkyl, with at least one of —R¹⁰ being hydrogen, and any one or more of —R¹, —R², —R³, and —R⁴ that is not —OR¹⁰ is selected from the group consisting of hydrogen, alkyl, aryl, alkyl aryl, aryl alkyl, alkoxy, hydroxyalkyl, —R⁵OOR⁶, —R⁵OR⁶, and —(R⁵O)$_n$R⁷, where —R⁵ is a divalent alkylene group, and —R⁶ and R⁷ are selected from the group consisting of hydrogen, alkyl, aryl, alkyl aryl, and aryl alkyl, and n is an integer in the range of 1-15.

The hydroxylated quinone antipolymerant can provide excellent antipolymerant activities similar to many nitroxyl-containing antipolymerants, and therefore does not necessarily require the simultaneous addition of a nitroxyl compound-containing antipolymerant for treatment of a hydrocarbon composition. In turn, this allows greater flexibility for inhibiting polymerization of a monomer composition, such as when the use of a nitroxyl-containing antipolymerant is not recommended. Compositions and methods of the disclosure are also advantageous in that they can avoid any release of NO$_x$ emissions that would otherwise result from the use of nitroxyl-containing antipolymerants. Therefore, the treated hydrocarbon composition can have no, or less than 50 ppm of a nitroxyl group containing antipolymerant, such as HTEMPO.

In embodiments, the hydroxylated quinone antipolymerant can be provided in a composition for addition to a composition containing a polymerizable monomer, or a composition that is capable of forming monomer. For example, the composition can include a solvent and antipolymerant component consisting essentially of the hydroxylated quinone of Formula I. Alternatively, the composition can include a solvent and the hydroxylated quinone antipolymerant, with the proviso that the composition includes little or no nitroxyl group-containing antipolymerant.

DETAILED DESCRIPTION

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

The disclosure provides methods and compositions that include a hydroxylated quinone antipolymerant to prevent unwanted formation of polymer in a hydrocarbon composition that includes monomer or a compound capable for forming a monomer. A hydrocarbon composition can include one or more hydrocarbon compounds such as derived from a petroleum product, which can be obtained from a subterranean reservoir, any product derived therefrom, or any mixture thereof.

The hydroxylated quinone antipolymerant compounds provide excellent antipolymerant activity similar to many nitroxyl-containing antipolymerants, and therefore methods of the disclosure do not necessarily require, and preferably do not include, the simultaneous addition of a nitroxyl compound-containing antipolymerant for treatment of a monomer stream. In turn, this allows greater flexibility for inhibiting polymerization of a monomer composition, such as when the use of a nitroxyl-containing antipolymerant is not recommended. Composition and methods of the disclosure are also advantageous in that they can avoid any release of NO$_x$ emissions that would otherwise result from the use of nitroxyl-containing antipolymerants.

A composition that includes the hydroxylated quinone antipolymerant and any one or more optional component can be in a desired form, such as in a liquid form, a dry form, or as a suspension or dispersion. The hydroxylated quinone antipolymerant can be in a desired physical state in the composition, such as in a dissolved state, in a partially dissolved state, in a suspended state, or in a dry mixture. Also, the hydroxylated quinone antipolymerant can be in desired forms in the composition, such as optionally in particulate forms. If the hydroxylated quinone antipolymerant is in a particulate form, the particles can optionally be described in terms of particle size (e.g., particles of a size range) and/or shape. The form of the composition and the state of the component(s) therein can be chosen by selection of the hydroxylated quinone antipolymerant, with an understanding of its physical properties.

The form of the composition and the state of the component(s) therein can also be affected by the inclusion of one or more optional components, such as a solvent, or solvent mixture, or other excipient compounds like surfactants, dispersants, etc. The form of the composition and the state of the components therein can also be affected by temperature, and composition properties may optionally be described in circumstances at a particular temperature (e.g., at a storage temperature such as 5° C. or below, at room temperature (25° C.), or at a temperature used for monomer synthesis and/or processing (e.g., about 100° C. or greater, about 150° C., about 175° C., etc.).

As noted, a hydroxylated quinone antipolymerant composition can include other components such as a solvent, surfactants, dispersants, etc. If an optional component is present in the composition, it may be described in terms of a weight amount relative to the hydroxylated quinone antipolymerant. The optional component(s) may be present in a weight amount greater than, in an amount about the same as, or an amount less than the hydroxylated quinone antipolymerant.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), greater than about 0.5% (wt), greater than about 0.1% (wt), or greater than about 0.01% (wt), of the total composition. A composition that consists essentially of a solid component that is the hydroxylated quinone antipolymerant (for example, dissolved in a solvent) can optionally include one or more other (e.g., solid) components but in an amount less than about 1% (wt) of the total composition weight. In a composition "consisting of" the recited components there is no other measurable amount of component other than the recited component. In some embodiments, a nitroxyl-containing antipolymerant can optionally be present in an amount of less than 1% (wt), less than 0.5% (wt), less than 0.1% (wt), or less than 0.01% (wt), of the total composition, and more preferably a nitroxyl-containing antipolymerant is not present in a detectable level in the composition.

"Antipolymerants" broadly refer to "polymerization inhibitors" and "polymerization retarders" which are compounds that generally inhibit or reduce the formation of polymers from one or more radically polymerizable compounds.

A "polymerization inhibitor," such as nitroxyl-containing compounds like HTEMPO, in the presence of polymerizable monomers, inhibits the formation of a polymer from those monomers during an induction time. After the induction time has lapsed, the polymer's formation occurs at substantially the same rate as it does in the absence of the polymerization inhibitor.

A "polymerization retarder," such as hydroxylated quinone compounds disclosed herein, does not exhibit an induction time, but instead once added to a polymerizable monomer composition reduces the rate at which the formation of the polymer occurs relative to the rate at which it would have formed in the absence of the polymerization retarder.

Polymerization inhibitors, as opposed to polymerization retarders, are generally consumed rapidly. Polymerization retarders, while they slow down the rate of polymerization reactions, are not as effective as polymerization inhibitors. Polymerization retarders, however, are usually not consumed as quickly as polymerization inhibitors.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of", the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

Compositions and methods of the disclosure include or use an antipolymerant that has a hydroxylated quinone chemistry. In embodiments, the hydroxylated quinone antipolymerant includes a partially unsaturated 6 carbon ring structure having at least two, and preferably two, carbonyl groups (C(O)), and at least one, and preferably two, hydroxyl groups attached to carbon ring atoms.

In some embodiments the hydroxylated quinone antipolymerant is a compound of Formula I:

wherein at least two of —$R^1$, —$R^2$, —$R^3$, and —$R^4$ are —$OR^{10}$, wherein $R^{10}$ is selected from the group consisting of hydrogen, alkyl, aryl, alkyl aryl, and aryl alkyl, with at least one of —$R^{10}$ being hydrogen, and any one or more of —$R^1$, —$R^2$, —$R^3$, and —$R^4$ that is not —$OR^{10}$ is selected from the group consisting of hydrogen, alkyl, aryl, alkyl aryl, aryl alkylene, alkoxy, hydroxyalkyl, —$R^5OOR^6$, —$R^5OR^6$, and —$(R^5O)_nR^7$, where —$R^5$ is a divalent alkylene group, and —$R^6$ and $R^7$ are selected from the group consisting of hydrogen, alkyl, aryl, alkyl aryl, and aryl alkyl, and n is an integer in the range of 1-15, an integer in the range of 1-10, or an integer in the range of 1-5.

In some compounds of Formula I, any one or more of —$R^1$, —$R^2$, —$R^3$, and —$R^4$ that is not —$OR^{10}$ can be selected from the group consisting of C1-C18 alkyl, aryl, alkyl aryl and aryl alkyl, alkoxy, hydroxyalkyl, —$R^5OOR^6$, —R$^5$OR$^6$, —(R$^5$O)$_n$R$^7$. In some compounds of Formula I, two of —R$^1$, —R$^2$, —R$^3$, and —R$^4$ that are not —OR$^{10}$ are independently selected from the group consisting of C1-C18 alkyl, aryl, alkyl aryl, aryl alkyl, alkoxy, hydroxyalkyl, —R$^5$OOR$^6$, —R$^5$OR$^6$, and —(R$^5$O)$_n$R$^7$. Any one or more of —R$^1$, —R$^2$, —R$^3$, and —R$^4$ can include a linear, branched, or cyclic hydrocarbon structure, or a combination of these structures.

In some compounds of Formula I, one of —R$^1$, —R$^2$, —R$^3$, and —R$^4$ that is not —OR$^{10}$ is selected from the group consisting of linear and branched C1-C12 alkyl, alkoxy, or hydroxyalkyl, and one of —R$^1$, —R$^2$, —R$^3$, and —R$^4$ that is not —OR$^{10}$ is —H. In some compounds of Formula I, two of —R$^1$, —R$^2$, —R$^3$, and —R$^4$ that are not —OH are —H.

Exemplary linear alkyl groups include methyl, ethyl, propyl, butyl, pentyl, hexyl, heptyl, octyl, nonyl, decyl, undecyl, and dodecyl. Exemplary branched alkyl groups include isobutyl, sec-butyl, tert-butyl, 1-, 2-, and 3-methylbutyl, 1,1-, 1,2-, or 2,2-dimethylpropyl, 1-ethyl-propyl, 1-, 2-, 3-, or 4-methylpentyl, 1,1-, 1,2-, 1,3-, 2,2-, 2,3-, or 3,3-dimethylbutyl, 1- or 2-ethylbutyl, 1-ethyl-1-methylpropyl, and 1,1,2- or 1,2,2-trimethylpropyl.

Exemplary cycloalkyl groups include those such as cyclopentyl, methylcyclopentyl, cyclohexyl, methylcyclohexyl, ethylcyclohexyl, propylcyclohexyl, etc. Exemplary partially or fully unsaturated hydrocarbon groups (e.g., aryl and aryl alkyl) include those such as phenyl, benzyl, methylphenyl, ethylphenyl, etc. Exemplary alkoxy groups include methoxymethyl, methoxyethyl, methoxypropyl, methoxybutyl, methoxypentyl, methoxyhexyl, ethoxymethyl, ethoxyethyl, etc. Exemplary hydroxyalkyl groups include hydoxymethyl, hydoxyethyl, hydoxypropyl, hydoxybutyl, hydoxypentyl, hydoxyhexyl, etc.

Alkyl aryl groups include those of Formula III: —R$^8$R$^9$$_y$, wherein R$^8$ is a divalent hydrocarbyl group (e.g., alkylene) and R$^9$ is an aryl group, and y is an integer of 1 or greater (e.g., 2, 3, etc.). In some embodiments, R$^8$ is C1-C12 alkylene, C1-C6 alkylene, and preferably C1, C2, or C3 alkylene. Exemplary alkyl aryl groups wherein y is 1 include benzyl, phenyl ethyl, phenyl propyl, and phenyl butyl. Exemplary alkyl aryl groups wherein y is 2 include dibenzyl, diphenyl ethyl, diphenyl propyl, and diphenyl butyl. Optionally, the aryl (R$^9$) group can be substituted, such as having an alkyl substituent, to form an alkyl aryl alkyl group.

In some embodiments the hydroxylated quinone antipolymerant is a compound of Formula II:

wherein —R$^2$ and —R$^4$ are not —OH and have the meanings set forth herein.

Exemplary hydroxylated quinone antipolymerants include 2,5-dihydroxy-1,4-benzoquinone, 3,6-dibenzhydryl-2,5-dihydroxybenzoquinone, and 3-benzhydryl-2,5-dihydroxybenzoquinone.

Hydroxylated quinone compounds are commercially available or can be prepared from any one or more methods as known in the art. For example, 2,5-dihydroxy-1,4-benzoquinone can be obtained from Sigma Aldrich (St. Louis, Mo.) or Santa Cruz Biotechnology (Dallas, Tex.). Hydroxylated benzoquinone derivatives can be made by reaction of a reactant such as 2,5-dihydroxy-1,4-benzoquinone with an alcohol in the presence of an acid. For example, the synthesis of aryl group-derivatized dihydroxybenzoquinone can be carried out using methods such as described in *Inorg. Chem.* 48, 9005-9017 (2009), in which 2,5-dihydroxy-1,4-benzoquinone is reacted with and benzhydrol in acetic acid with concentrated sulfuric acid. Compounds such as 3,6-dibenzhydryl-2,5-dihydroxybenzoquinone and 3-benzhydryl-2,5-dihydroxybenzoquinone can be obtained.

An amount of the hydroxylated quinone antipolymerant and any other (optional) component in a composition can be described in various ways, such as by a weight percentage (% wt.) or by molar amount of hydroxylated quinone antipolymerant in the composition. When other components are used along with the hydroxylated quinone antipolymerant, such compounds can also be described in terms of weight ratios, or in terms of relative amounts to one another, in a composition.

As discussed herein, a hydroxylated quinone can be used without, or with minimal nitroxyl group containing antipolymerant. If a nitroxyl group containing antipolymerant is included, it can be present in very small amounts, such as in a composition comprising polymerizable monomer, wherein the nitroxyl group containing antipolymerant is not present at all, or present in a very small amount (less than 50 ppm).

For example, in a composition comprising polymerizable monomer and the hydroxylated quinone antipolymerant, a nitroxyl group containing antipolymerant can optionally be present in an amount of less than 50 ppm, less than 25 ppm, less than 10 ppm, less than 5 ppm, less than 2.5 ppm, less than 2 ppm, less than 1.5 ppm, less than 1 ppm, less than 0.75 ppm, or less than 0.5 ppm.

Nitroxyl group-containing compounds trap propagating monomer radicals in thermally unstable species and inhibit polymerization. A nitroxyl/nitroxide group, which can also be referred to as an amine-N-oxide group, is a functional group including an NO bond and side groups attaching to the nitrogen. Nitroxide (nitroxyl) radicals are oxygen-centered radicals with the free electron delocalized over the N—O bond. Nitroxide-containing polymerization inhibitors can include N—O resonance structures that contribute to the stability of nitroxide radicals.

Exemplary nitroxide-containing compounds which can be excluded from compositions from the disclosure, or are used in limited amounts, include, but are not limited to: 2,2,6,6-tetramethylpiperidinyl-1-oxyl (TEMPO), 4-hydroxy-2,2,6,6-tetramethylpiperidinyl-1-oxyl (HTMPO), 4-oxo-2,2,6,6-tetramethylpiperidinyl-1-oxyl (OTEMPO), di-tert-butyl nitroxyl, 1-oxyl-2,2,6,6-tetramethyl-4-n-propoxypiperidine, 1-oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)piperidine, 1-oxyl-2,2,6,6-tetramethylpiperidin-4-yl stearate, 1-oxyl-2,2,6,6-tetramethylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6- tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N-(1-oxyl-2,2,6,6-tetramethylpiperidin-4-yl)-caprolactam, N-(1-oxyl-2,2,6,6-tetramethylpiperidin-4-yl)-dodecylsuccinimide, 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, and mixtures thereof. (See, for example, U.S. Pat. No. 9,266,797.) Any of these compounds can be present at very low amounts (less than 50 ppm, 25 ppm, 10 ppm, etc., as described herein) in a polymerizable monomer composition, or can be excluded from the composition altogether.

Other exemplary nitroxide-containing compounds include two or three nitroxyl groups. Such compounds may be bis- or tris-compounds. Exemplary bis-nitroxide and tris-nitroxide polymerization inhibitor compound include bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, 2,4,6-tris-[N-butyl-N-(1-oxyl-2,2,6,6-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), and mixtures thereof. (See, for example, U.S. Pat. No. 9,266,797.) Any of these compounds can be present at very low amounts (less than 50 ppm, 25 ppm, 10 ppm, etc., as described herein) in a polymerizable monomer composition, or can be excluded from the composition altogether.

Other types of compounds that are different from a nitroxyl group containing-compound can also optionally be excluded from the hydroxylated quinone composition, or used in very low amounts. For example, in some embodiments, the composition optionally excludes, or uses very low amounts of zinc chloride, such as less than 0.1% (wt), less than 0.01% (wt), less than 0.001% (wt), or less than 0.0001% (wt), or no detectable amount of zinc chloride. As another example, in some embodiments, the composition optionally excludes, or uses very low amounts of tetrahydroquinoline, such as less than 0.1% (wt), less than 0.01% (wt), less than 0.001% (wt), or less than 0.0001% (wt), or no detectable amount of tetrahydroquinoline.

The hydroxylated quinone antipolymerant can be present in a composition with a solvent, or a combination of solvents. A solvent or solvent combination can be chosen so that one or more of the hydroxylated quinone antipolymerant is soluble in the solvent or solvent combination. If the hydroxylated quinone antipolymerant is a liquid at ambient conditions, a miscible solvent can be chosen.

Useful solvents include any solvent in which the hydroxylated quinone antipolymerant is soluble or can be stably suspended. In some embodiments, a solvent or solvent combination can be selected from water soluble or water miscible solvents such glycol-based solvents and hydrophobic or hydrocarbon solvents such as aromatic solvents, paraffinic solvents, or mixtures of both.

Exemplary glycol solvents include, but are not limited to, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, which contains primarily Butyl CARBITOL™, which consists primarily of ethylene glycol monobutyl ether may be used and are available from DOW.

Other exemplary hydrophobic or hydrocarbon solvents include heavy aromatic naphtha, toluene, ethylbenzene, isomeric hexanes, benzene, xylene, such as ortho-xylene, para-xylene, or meta-xylene, and mixtures of two or more thereof.

In some embodiments, the solvent is selected from glycol and aromatic naphtha and combinations thereof.

The amount of hydroxylated quinone antipolymerant (with one or more optional components), in a solvent, or a combination of solvents, can be described one or more ways, such as by the percent solids (wt) of the component(s) in the composition, or by the molar amount of solid components in the composition.

As an example, a stock composition of hydroxylated quinone antipolymerant can be dissolved in a solvent to a concentration of about at least about 0.00001% (wt), at least about 5% (wt), such as in an amount in the range from about 0.00001% (wt) to about 50% (wt).

An amount of the stock composition including hydroxylated quinone antipolymerant can be added to a monomer-containing composition or composition capable of forming monomer, to provide the antipolymerant at a concentration effective to inhibit polymerization of monomer.

The polymerizable monomer that is subjected to polymerization inhibition by the hydroxylated quinone can include a vinyl or ethylenically unsaturated group. For example, the components of the hydroxylated quinone antipolymerant and any optional component can be added to a composition that includes one or more of the following polymerizable monomers: acrolein, acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyl acetate, vinyltoluene, and vinylpyridine.

The polymerizable monomer can be present in a crude mixture of compounds, a semi-refined mixture of compounds, or a fully-refined mixture of compounds. For example, the hydroxylated quinone antipolymerant can be added to a process stream that includes the polymerizable monomer and one or more other components that are different than the polymerizable monomer. In methods, the hydroxylated quinone antipolymerant can be added before, during, or after, (or combinations thereof) a processing step, such as distillation, wherein compounds in the composition are separated from one another. The hydroxylated quinone antipolymerant can inhibit polymerization of monomer at any one or more stages in a processing system, and therefore reduce or prevent fouling of equipment.

Alternatively, the hydroxylated quinone antipolymerant can be added to a process stream that includes a compound capable of forming into a polymerizable monomer (e.g., a monomer precursor), such as ethylbenzene which is a precursor to styrene. For example, in embodiments, a composition may include a compound that is capable of forming a polymerizable monomer as an unwanted by-product. In this situation, the presence of the hydroxylated quinone antipolymerant can inhibit polymerization of the monomer if it does form as a by-product, and can therefore reduce or prevent fouling of equipment.

In modes of practice, the hydroxylated quinone antipolymerant is introduced into a monomer-containing composition or a composition that includes a compound capable of forming a polymerizable monomer, at a desired concentration effective to inhibit monomer polymerization. The hydroxylated quinone antipolymerant can be added to a composition that includes one or more polymerizable monomers, or one or more compounds that are capable of forming polymerizable monomers. The monomer(s) and/or monomer-forming compound(s) can be present at any concentration in the composition, such as in very small amounts (ppm) or amounts wherein the monomer(s) and/or monomer-forming compound(s) are present in bulk amounts in the composition (e.g., 50% (wt) or greater). Exemplary ranges are from any one of about 5 ppm, about 200 ppm, about 50 ppm, or about 100 ppm (0.1%) to, about 10% (wt), about 25% (wt), about 50% (wt), or about 75% (wt).

The amount of hydroxylated quinone antipolymerant in a composition that includes monomer(s) and/or monomer-forming compound(s) can be chosen based on the monomer/compound type, the amount of monomer/compound in the composition, the type of composition having the monomer/compound, any processing, treatment, or storage conditions for the composition, and the presence of any one or more optional compounds that are different than the hydroxylated quinone antipolymerant and that are added to the composition. The hydroxylated quinone antipolymerant can be added to the composition in an amount to provide a desired level of polymerization inhibition.

In embodiments, the hydroxylated quinone antipolymerant can be used in an amount of at least about 0.10 ppm, such as in the range of about 0.10 ppm to about 50,000 ppm, in the range of about 0.10 ppm to about 25,000 ppm, about 0.10 ppm to about 10,000 ppm, about 5 ppm to about 5,000 ppm, about 25 ppm to about 2,500 ppm, about 50 ppm to about 1,000 ppm, about 50 ppm to about 1,000 ppm, about 75 ppm to about 500 ppm, about 100 ppm to about 300 ppm, about 125 ppm to about 275 ppm, or about 150 to about 250 ppm.

In some modes of practice the hydroxylated quinone antipolymerant is used before or after a polymerizable monomer-containing composition is treated with a polymerization inhibitor that is different than the hydroxylated quinone, such as a nitroxide-containing polymerization inhibitor (e.g., HTEMPO, etc.). In some modes of practice, the hydroxylated quinone antipolymerant is added to a polymerizable monomer composition after the composition has been treated with a nitroxide-containing polymerization inhibitor, and the inhibitor has been at least substantially consumed or has otherwise at least lost most of its inhibitor activity. For example, a nitroxide-containing polymerization inhibitor can be added to a monomer-containing composition at a first time point and then the composition can be monitored to determine any increase in the formation of polymer and/or presence of inhibitor, and if there is an increase in formation of polymer or reduction in inhibitor, the hydroxylated quinone antipolymerant can be added at a second time point to maintain inhibition of polymerization.

In other modes of practice, the hydroxylated quinone antipolymerant can be added to a monomer-containing composition at a first time point, and then one or more other compounds useful for inhibiting polymerization that is different than the hydroxylated quinone can be added to the composition at one or more later time point(s) (e.g., second, third, etc.).

The hydroxylated quinone antipolymerant can be added to a polymerizable monomer composition in any one or more different ways, such as addition of the antipolymerant in single dose, continuous addition, semi-continuous addition, intermittent addition, or any combination of these methods. In a continuous addition, the hydroxylated quinone antipolymerant can be added at a constant or variable rate. The mode or modes of addition of the hydroxylated quinone antipolymerant can be chosen based on the polymerizable monomer-containing composition and how it is being stored, processed, or otherwise treated. For example, in a process stream involving the movement and separation of polymerizable monomer, or a compound that can form a polymerizable monomer, from other components such as a distillation apparatus, the hydroxylated quinone antipolymerant can be added in a continuous or semi-continuous manner to account for new monomer or monomer precursor constantly being introduced.

The term "fouling" refers to the formation of polymers, prepolymers, oligomer and/or other materials which would become insoluble in and/or precipitate from a stream and deposit on equipment under conditions of operating the equipment. In turn, the hydroxylated quinone antipolymerant can be referred to as an "antifoulant" as it prevents or reduces such formation.

Optionally, the ability of the compositions of the disclosure to inhibit polymerization can be described relative to a composition that does not include the hydroxylated quinone antipolymerant, or that includes a comparative compound. The effect of the hydroxylated quinone antipolymerant can be understood by measuring the formation of a polymer (e.g., polystyrene) in a monomer (e.g., styrene) composition over time, in the presence of a composition that includes the hydroxylated quinone antipolymerant as compared to one that does not include the hydroxylated quinone antipolymerant, or that uses an antipolymerant having chemistry that is different than one of the disclosure.

For example, a composition of the disclosure with a hydroxylated quinone antipolymerant can inhibit polymerization of monomer by more than 50%, by more than 60%, by more than 70%, by more than 80%, by more than 85%, by more than 90%, by more than 92.5%, by more than 95%, or by more than 97%, as compared to a composition with a non-hydroxylated quinone (e.g., a di-butyl-1,4-benzoquinone), under the same conditions.

The hydroxylated quinone antipolymerant can be used in conjunction with compositions containing polymerizable monomers and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by monomer polymerization. This term also includes sets of these components where more than one of the components is part of a "system."

In one preferred method of use, a composition of the disclosure with hydroxylated quinone antipolymerant and solvent (e.g., glycol) is used with a process that involves a distillation tower that is used to separate and purify vinylic monomers, such as styrene. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity. Optionally, the hydroxylated quinone antipolymerant is used along with one or more secondary components such as stabilizers like butylated hydroxytoluene (BHT) and tert-butylcatechol (TBC). In an exemplary mode of practice these components are used in a distillation tower that is used to separate and purify vinylic monomers.

The hydroxylated quinone antipolymerant-containing composition can be introduced into a stream leading from the reaction bed to the distillation tower, or can be directly added to the distillation tower. The compositions can be added prior to heating the monomer composition or while heating the monomer composition in the distillation tower. In embodiments, the hydroxylated quinone antipolymerant compound has a boiling point that is higher than that of the desired compound or distillate (e.g., a monomer such as styrene) subject to distillation tower and during the distillation process the desired compound is separated from the hydroxylated quinone antipolymerant compound by virtue of temperature difference. In embodiments, the boiling point difference between the compound of interest and the hydroxylated quinone antipolymerant is about 10° C. or greater, about 15° C. or greater, about 20° C. or greater, about 25° C. or greater, about 30° C. or greater, about 35° C. or greater, about 40° C. or greater, about 45° C. or greater, or about 50° C. or greater.

Alternatively, or in addition to adding the hydroxylated quinone antipolymerant during a distillation process, the composition can be optionally or further added to a distillation effluent stream, such as a purified styrene stream. Optionally, another antipolymerant can be added to a distillation effluent stream prior to or along with the hydroxylated quinone antipolymerant.

The hydroxylated quinone antipolymerant, optionally used in combination with one or more other components, can be used with any "hydrocarbon process stream" which can include unsaturated monomer in order to stabilize the stream during transportation and storage. In some modes of practice, the hydroxylated quinone antipolymerant can be used in conjunction with a "petroleum product" which can include a hydrocarbon product obtained from a subterranean reservoir, any product derived therefrom, or any mixture thereof.

Polymerizable monomers are found in or can be chemically derived from petroleum products. Nonlimiting examples of petroleum products include but are not limited to crude oil, reduced crude oil, crude distillate, heavy oil, or bitumen, hydrotreated oil, refined oil, byproducts of petroleum product processing such as pyrolysis, hydrotreating, or phase separation, or mixtures of two or more of these. A liquid petroleum product is a petroleum product that is substantially a liquid at 20° C.

The hydroxylated quinone antipolymerant can be added to or can be present in a "petroleum process stream" which refers to any petroleum product disposed within petroleum process equipment in fluid contact with an interior surface thereof.

The petroleum process stream can include, or can be capable of forming as a by-product, one or more polymerizable monomer. The process stream may be substantially static, such as a petroleum product disposed within in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a man-made item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including the hydroxylated quinone antipolymerant are thermally stable and have antipolymerant activity in processing streams or other polymerizable monomer-containing compositions at temperatures of about 20° C. to about 400° C., for example about 100° C. to about 400° C., about 100° C. to about 350° C., about 100° C. to about 300° C., about 100° C. to about 250° C., about 100° C. to about 200° C., or about 100° C. to about 150° C.

In embodiments, compositions including hydroxylated quinone antipolymerant can be introduced into a composition with a polymerizable monomer, such as a liquid petroleum process stream in a batch-wise, a continuous, or a semi-continuous manner. In some embodiments, the hydroxylated quinone antipolymerant (and any other optional component) are introduced manually; and in other embodiments, their introduction is automated. In embodiments, the amount of the hydroxylated quinone antipolymerant introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the hydroxylated quinone antipolymerant is added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. In embodiments, the antipolymerant is added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein.

Equipment containing the polymerizable monomer-containing compositions that are treated with the hydroxylated quinone antipolymerant and any other optional component can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The hydroxylated quinone antipolymerant can also inhibit unwanted polymerization and fouling of the process equipment in a primary fractionation process, light ends fractionation, non-aromatic halogenated vinyl fractionation and stabilization, process-gas compression, dilution steam system, caustic tower, quench water tower, quench water separator (pyrolysis gasoline), butadiene extraction, propane dehydrogenation, diesel and petrol fuel stabilization, olefin metathesis, styrene purification, hydroxyhydrocarbon purification, stabilization of vinylic monomers during transportation and storage, or delays the polymerization of resins and compositions comprising ethylenically unsaturated species.

The hydroxylated quinone antipolymerant can be added at any given point in a process and at one or more locations. For example, an antipolymerant composition can be added directly at the interstage coolers or compressors or upstream of the inter-coolers or compressors. The hydroxylated quinone antipolymerant can be added continuously or intermittently to the process equipment as required preventing or reducing fouling.

The hydroxylated quinone antipolymerant can be introduced to desired systems by any suitable method. For example it may be added in neat or a dilute solution. In some embodiments, a composition containing the hydroxylated quinone antipolymerant can be applied as a solution, emulsion, or dispersion that is sprayed, dripped, poured or injected into a desired opening within a system or onto the process equipment or process condensate. In some embodiments, the composition may be added with a washoil or an attemperation water.

After introducing the composition to process equipment, treated process equipment can be observed to have less deposition on equipment than in process equipment without addition of the composition. Reduction or prevention in fouling can be evaluated by any known method or test. In some embodiments, the reduction or prevention of fouling can be accessed by measuring the time it takes for a sample with and without the antifoulant composition to gel.

Example 1

Performance of 2,5-DHBQ in Styrene

To screen the antipolymerant performance of 2,5-dihydroxy-1,4-benzoquinone (2,5-DHBQ), a static method was used. A 200 ppm solution of 2,5-DHBQ was prepared in styrene in which 4-tert-butylcatechol (TBC) stabilizer was removed just before the treatment with 2,5-DHBQ. An alumina column was used for removal of said stabilizer. A solution consisting of 200 ppm of 2,5-DHBQ was prepared by dissolving 0.0715 g in the freshly de-inhibited styrene to yield 350 g of solution. To each of twenty-four Ace Glass #15 threaded pressure tubes equipped with PTFE screw caps and fluoroelastomer (FETFE) O-rings were charged 10 mL of the solution. For each test tube, the dissolved oxygen was purged out of the solutions by sparging with nitrogen for 2 minutes. Following the sparge, each tube was immediately sealed and the solution kept under a nitrogen headspace. The tubes were loaded into a heating block that had been preheated to 120° C. After 30 minutes, and every 15 minutes thereafter, four tubes were retrieved from the block and the polymerization reaction quenched by cooling in an ice bath. The cooled polymer solutions were immediately diluted with toluene. A proprietary method was also used to measure the polymer.

Figure 1:
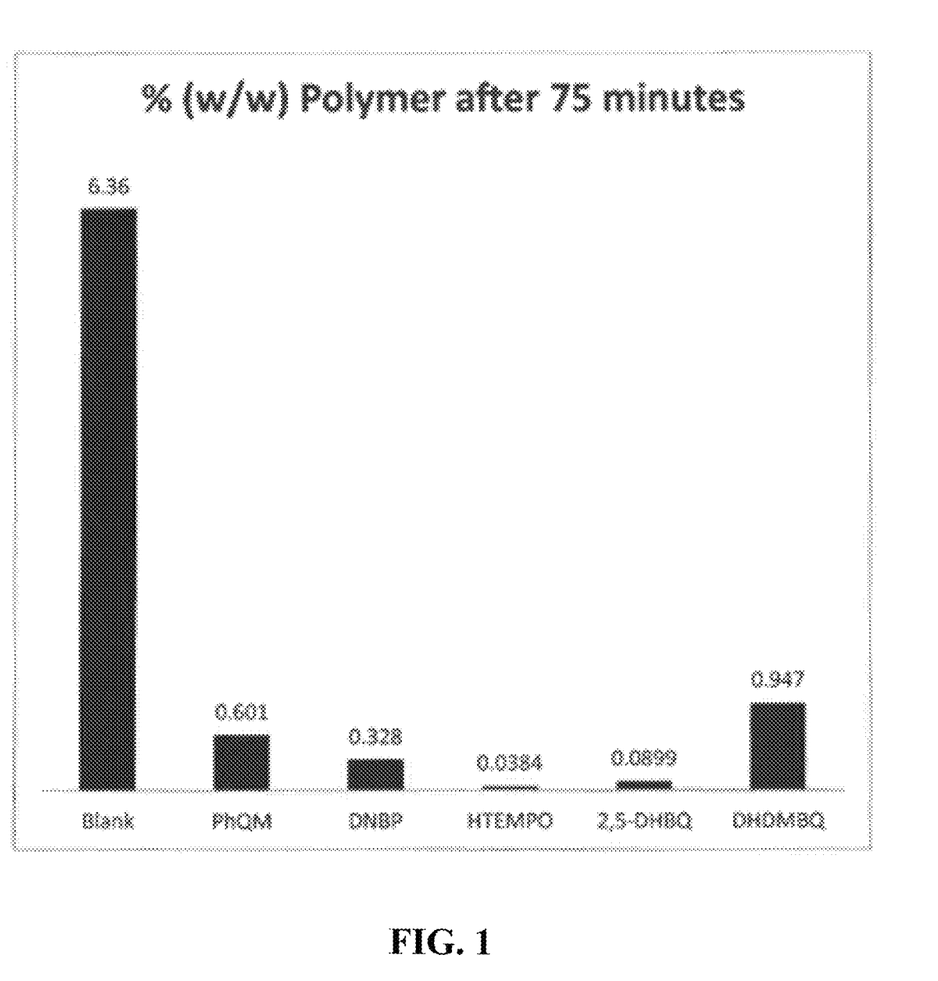
FIG. 1 is a graph of the amount of polystyrene polymer formed from styrene monomer solutions in the presence of various antipolymerants including 2,5-DHBQ.

The antipolymerant performance of 2,5-DHBQ was compared to HTEMPO (4-hydroxy-2,2,6,6-tetramethylpiperidinyl-1-oxyl); 7-phenyl quinone methide (7-PhQM); 2,4-dinitro-sec-butylphenol (DNBP); and 2,5-dihydroxy-3,6-dimethoxy-p-benzoquinone (DHDMBQ), all at 200 ppm in styrene. Table 1 provides results of the study, which are also shown in FIG. 1.

TABLE 1

Performance of antipolymerants in styrene at 200 ppm.

| Time (minutes) | % Polystyrene (w/w) | | | | | |
|---|---|---|---|---|---|---|
| | Blank | 7-PhQM | DNBP | HTEMPO | 2,5-DHBQ | DHDMBQ |
| 30 | 1.96 | 0.199 | 0.0877 | 0.0177 | 0.0300 | 0.0668 |
| 45 | 3.24 | 0.331 | 0.144 | 0.0227 | 0.0426 | 0.174 |
| 60 | 4.72 | 0.531 | 0.329 | 0.0314 | 0.0592 | 0.364 |
| 75 | 6.36 | 0.601 | 0.328 | 0.0384 | 0.0899 | 0.947 |
| 90 | 7.78 | 0.864 | 0.590 | 0.0426 | 0.130 | 1.23 |
| 105 | 10.57 | 1.05 | 0.809 | 0.0586 | 0.329 | 1.66 |
| 120 | | 1.22 | 1.01 | 0.0632 | 0.463 | 3.54 |

Results show that 2,5-DHBQ, by itself, inhibited polymerization of styrene to a significant extent and performed much better than 7-PhQM, DNBP, and DHDMBQ.

Example 2

Performance of 2,5-DHBQ in Methyl Methacrylate

A solution consisting of 20 ppm of benzoyl peroxide in methyl methacrylate was prepared. To each of twenty-four Ace Glass #15 threaded pressure tubes equipped with PTFE screw caps and fluoroelastomer (FETFE) O-rings were added 10 mL aliquots of this solution. The dissolved oxygen removed and kept out of the solutions as described in Example 1. Polymerization reactions were performed by loading the tubes into a heating block preheated to 100° C. Following 30 minutes, and every 15 minutes after that, four tubes were retrieved from the block and an ice bath used to quench the polymerization reactions. The cooled polymer solutions were immediately diluted with toluene and then the polymer content immediately measured using a proprietary method.

A solution consisting of 0.58 mmolal of 2,5-DHBQ and 20 ppm of benzoyl peroxide in methyl methacrylate was prepared. The procedure in Example 1 was used to remove oxygen, polymerize the solutions, and measure the amount of polymer formed.

The antipolymerant performance of 2,5-DHBQ was compared to HTEMPO (4-hydroxy-2,2,6,6-tetramethylpiperidinyl-1-oxyl) and para-benzoquinone (pBQ), all at 0.58 mmolal in methyl methacrylate.

Figure 2:
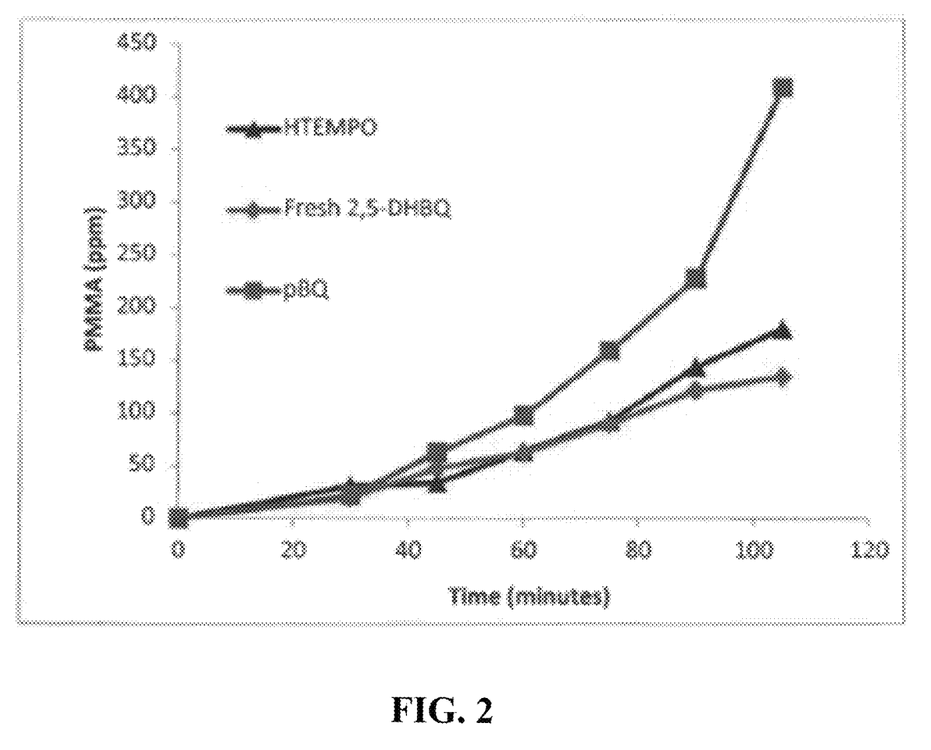
FIG. 2 is a graph of the amount of poly(methyl)methacrylate (PMMA) formed from methylmethacrylate monomer solutions in the presence of various antipolymerants including 2,5-DHBQ.

Table 2 provides results of the study, which are also shown in FIG. 2.

TABLE 2

Performance of antipolymerants in methyl methacrylate at 0.580 mmol.

| | Poly(methyl methacrylate) (ppm) | | | |
|---|---|---|---|---|
| Time (minutes) | Blank | HTEMPO | 2,5-DHBQ | pBQ |
| 30 | 18588 | 31 | 20 | 22 |
| 45 | 48550 | 34 | 48 | 63 |
| 60 | 80231 | 64 | 63 | 98 |
| 75 | 83625 | 93 | 90 | 159 |
| 90 | 93993 | 144 | 122 | 228 |
| 105 | | 180 | 135 | 409 |

Results show that 2,5-DHBQ, by itself, inhibited polymerization of methyl methacrylate to a significant extent and remarkably performed better than HTEMPO and pBQ.

What is claimed is:

1. A method for inhibiting the polymerization of monomers in a composition comprising a polymerizable monomer or polymerizable monomer-forming compound, the method comprising:
adding a hydroxylated quinone antipolymerant to the composition comprising polymerizable monomer or capable of forming a polymerizable monomer, the antipolymerant being a compound of Formula I:

(I)

wherein two or three of —$R^1$, —$R^2$, —$R^3$, and —$R^4$ are —$OR^{10}$, wherein $R^{10}$ is selected from the group consisting of hydrogen, alkyl, aryl, alkyl aryl, and aryl alkyl, with at least one of —$R^{10}$ being hydrogen, and one or two of —$R^1$, —$R^2$, —$R^3$, and —$R^4$ that is or are not —$OR^{10}$ is or are —$R^8R^9_y$, wherein $R^8$ is a hydrocarbyl group, $R^9$ is an aryl group, and y is an integer, and wherein any of —$R^1$, —$R^2$, —$R^3$, and —$R^4$, that is not —$OR^{10}$ or —$R^8R^9_y$ is selected from the group consisting of hydrogen, alkyl, aryl, alkyl aryl, aryl alkyl, alkoxy, hydroxyalkyl, —$R^5OOR^6$, —$R^5OR^6$, and —$(R^5O)_nR^7$, where —$R^5$ is a divalent alkylene group, and —$R^6$ and $R^7$ are selected from the group consisting of hydrogen, alkyl, aryl, alkyl aryl, and aryl alkyl, and n is an integer in the range of 1-15.

2. The method of claim 1 wherein any of —$R^1$, —$R^2$, —$R^3$, and —$R^4$ that is not —$OR^{10}$ or —$R^8R^9_y$ is selected from the group consisting of C1-C18 alkyl, aryl, alkyl aryl, and aryl alkyl.

3. The method of claim 1 wherein two of —$R^1$, —$R^2$, —$R^3$, and —$R^4$ that are not —$OR^{10}$ are —$R^8R^9_y$, wherein $R^8$ is a divalent hydrocarbyl group, and y is 1.

4. The method of claim 1 wherein any of —$R^1$, —$R^2$, —$R^3$, and —$R^4$ that is not —$OR^{10}$ or —$R^8R^9_y$ is:
(a) selected from the group consisting of methyl, ethyl, propyl, butyl, pentyl, hexyl, heptyl, octyl, nonyl, decyl, undecyl, and dodecyl;
(b) selected from the group consisting of isobutyl, sec-butyl, tert-butyl, 1-, 2-, and 3-methylbutyl, 1,1-, 1,2-, and 2,2-dimethylpropyl, 1-ethyl-propyl, 1-, 2-, 3-, and 4-methylpentyl, 1,1-, 1,2-, 1,3-, 2,2-, 2,3-, and 3,3-dimethylbutyl, 1- and 2-ethylbutyl, 1-ethyl-1-methyl-propyl, and 1,1,2- and 1,2,2-trimethylpropyl;
(c) selected from the group consisting of cyclopentyl, methylcyclopentyl, cyclohexyl, methylcyclohexyl, ethylcyclohexyl, and propylcyclohexyl;
(d) selected from the group consisting of phenyl, benzyl, methylphenyl, and ethylphenyl;
(e) selected from the group consisting of methoxymethyl, methoxyethyl, methoxypropyl, methoxybutyl, methoxypentyl, methoxyhexyl, ethoxymethyl, and ethoxyethyl; or
(f) selected from the group consisting of hydoxymethyl, hydoxyethyl, hydoxypropyl, hydoxybutyl, hydoxypentyl, and hydoxyhexyl.

5. The method of claim 1 wherein the antipolymerant is compound of Formula II:

6. The method of claim 5 wherein the antipolymerant is 3,6-dibenzhydryl-2,5-dihydroxybenzoquinone or 3-benzhydryl-2,5-dihydroxybenzoquinone.

7. The method of claim 1 wherein the antipolymerant is present in the composition in an amount in the range of 0.1 ppm to 50000 ppm.

8. The method of claim 7 wherein the antipolymerant is present in the composition in an amount in the range of 5 ppm to 5000 ppm.

9. The method of claim 8 wherein the antipolymerant is present in the composition in an amount in the range of 75 ppm to 500 ppm.

10. The method of claim 1 wherein the polymerizable monomer comprises a vinyl or ethylenically unsaturated group.

11. The method of claim 10 wherein the polymerizable monomer is selected from the group consisting of acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyltoluene, vinylpyridine, divinylbenzenze, ethylene, acetylene, methylacetylene, vinylacetylene, propylene, butene, butyne, butadiene, cyclopentadiene, dicyclopentadiene, and indene.

12. The method of any of claim 1 wherein the composition comprises styrene or ethylbenzene.

13. The method of claim 1 wherein the composition is derived from a petroleum stream.

14. The method of claim 1 wherein the composition comprises hydrocarbons that are different than, or precursors to, the polymerizable monomers.

15. The method of claim 1 which is performed during purification or processing of one or more components of the composition.

16. The method of claim 1 wherein the composition has no, or less than 5 ppm of a nitroxyl group containing antipolymerant.

17. The method of claim 1 wherein the composition has no, or less than 1 ppm of a nitroxyl group containing antipolymerant.

18. The method of claim 17 wherein the composition has no, or less than 0.5 ppm of a nitroxyl group-containing antipolymerant.

19. The method of claim 16 wherein the inhibitor is a nitroxyl group-containing compound selected from the group consisting of 2,2,6,6-tetramethylpiperidinyl-1-oxyl (TEMPO), 4-hydroxy-2,2,6,6-tetramethylpiperidinyl-1-oxyl (HTMPO), 4-oxo-2,2,6,6-tetramethylpiperidinyl-1-oxyl (OTEMPO), or a combination thereof.

20. The method of claim 1 wherein y is 1, 2, or 3.

\* \* \* \* \*